United States Patent

Maurer et al.

[11] 4,261,983
[45] Apr. 14, 1981

[54] COMBATING PESTS WITH O-ALKYL-O-(2-CYCLOPROPYL-PYRIMIDIN-4-YL)-THIONO)(THIOL)-PHOSPHORIC(PHOSPHONIC) ACID ESTERS AND ESTER-AMIDES

[75] Inventors: Fritz Maurer; Rolf Schröder, both of Wuppertal; Ingeborg Hammann, Cologne; Wolfgang Behrenz, Overath; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 54,066

[22] Filed: Jul. 2, 1979

[30] Foreign Application Priority Data

Jul. 20, 1978 [DE] Fed. Rep. of Germany ....... 2831852

[51] Int. Cl.³ .................. A01N 57/16; A01N 57/24; A01N 57/32; C07F 9/65
[52] U.S. Cl. ................................. 424/200; 544/243; 544/319
[58] Field of Search ................. 544/243; 424/200

[56] References Cited

U.S. PATENT DOCUMENTS

| 4,012,506 | 3/1977 | Balke et al. .............. 424/200 |
| 4,150,159 | 4/1979 | Maurer et al. ............ 424/200 |
| 4,155,999 | 5/1979 | Maurer et al. ............ 424/200 |

FOREIGN PATENT DOCUMENTS 910652 5/1954 Fed. Rep. of Germany .

Primary Examiner—Donald G. Daus
Assistant Examiner—Diana G. Rivers
Attorney, Agent, or Firm—Sprung, Felfe, Horn, Lynch & Kramer

[57] ABSTRACT

O-Alkyl-O-(2-cyclopropyl-pyrimidin-4-yl)-thiono(thiol)-phosphoric(phosphonic) acid esters and ester-amides of the formula

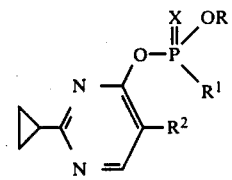

in which
R is alkyl,
$R^1$ is alkyl, alkoxy, alkylthio, alkylamino or phenyl,
$R^2$ is hydrogen, alkyl or halogen, and
X is oxygen or sulphur, which possess arthropodicidal and nematicidal properties.

9 Claims, No Drawings

COMBATING PESTS WITH O-ALKYL-O-(2-CYCLOPROPYL-PYRIMIDIN-4-YL)-THIONO)(THIOL)-PHOSPHORIC(PHOSPHONIC) ACID ESTERS AND ESTER-AMIDES

The present invention relates to and has for its objects the provision of particular new O-alkyl-O-(2-cyclopropylpyrimidin-4-yl)-(thiono)(thiol)-phosphoric(phosphonic)acid esters and ester-amides which possess arthropodicidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known that certain pyrimidinyl-thiono(thiol)-phosphoric acid esters, for example O,O-diethyl-O-(2-iso-propyl-6-methyl-pyrimidin-4-yl)-thionophosphoric acid ester, O-ethyl-S-n-propyl-O-(2-iso-propyl-6-methyl-pyrimidin-4-yl)-thiono-thiol-phosphoric acid ester and O,O-diethyl-O-(2-methylthio-6-methyl-pyrimidin-4-yl)-thionophosphoric acid ester, are insecticidally, acaricidally and nematicidally active (see German patent specification No. 910,652 and U.S. Pat. No. 3,951,975, issued Apr. 20, 1976). However, the action of these compounds is not always satisfactory, especially when using low amounts and low concentrations.

The present invention now provides, as new compounds, the 2-cyclopropyl-pyrimidin-4-yl(thiono)(thiol)-phosphoric(phosphonic) acid esters and ester-amides of the general formula

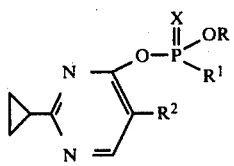

in which
R represents alkyl,
R¹ represents alkyl, alkoxy, alkylthio, alkylamino or phenyl,
R² represents hydrogen, alkyl or halogen and
X represents oxygen or sulphur.
Preferably, in formula (I),
R represents straight-chain or branched alkyl with 1 to 5 (especially with 1 to 3) carbon atoms,
R¹ represents straight-chain or branched alkyl with 1 to 5 (especially with 1 to 3) carbon atoms, straight-chain or branched alkoxy, alkylthio or alkylamino with 1 to 5 (especially with 1 to 3) carbon atoms per alkyl radical, or phenyl, and
R² represents hydrogen, straight-chain or branched alkyl with 1 to 5 (especially with 1 to 3) carbon atoms, chlorine or bromine.

Surprisingly, the 2-cyclopropyl-pyrimidin-4-yl-(thiono)(thiol)-phosphoric(phosphonic) acid esters and ester-amides according to the invention exhibit a better action as pesticides, especially a better insecticidal, nematicidal and acaricidal action, than the corresponding compounds of analogous structure and of the same type of action, known from the prior art. The products according to the present invention thus represent a valuable enrichment of the art.

The invention also provides a process for the preparation of a 2-cyclo-propyl-pyrimidin-4-yl(thiono) (thiol)-phosphoric(phosphonic) acid ester or ester-amide of the formula (I), in which a (thiono)(thiol)phosphoric(phosphonic) acid ester halide or (thiono)-phosphoric acid ester-amide halide of the general formula

in which
R, R¹ and X have the above-mentioned meanings and
Hal represents chlorine or bromine,
is reacted with a 2-cyclopropyl-4-hydroxy-pyrimidine of the general formula

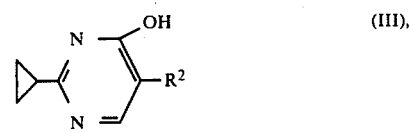

in which
R² has the above-mentioned meaning,
if appropriate in the presence of an acid acceptor and, if appropriate, in the presence of a diluent.

If, for example, O-methyl-ethanephosphonic acid ester chloride and 2-cyclopropyl-5-n-propyl-4-hydroxypyrimidine are used as starting materials, the reaction of these compounds can be outlined by the following equation:

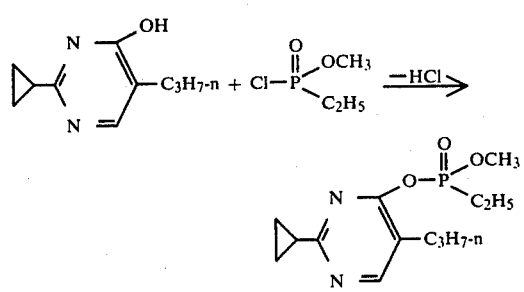

The (thiono)(thiol)-phosphoric(phosphonic) acid ester halides and (thiono)-phosphoric acid ester-amide halides to be used as starting materials are defined by the formula (II). Preferably, in this formula, R, R¹ and X have the meanings stated to be preferred in connexion with formula (I) and Hal represents chlorine.

The following may be mentioned specifically as examples of the starting compounds of the formula (II): O-methyl-, O-ethyl-, O-n-propyl- and O-iso-propylmethane-, -ethane-, -propane- and -phenyl-phosphonic acid ester chloride and the corresponding thiono analogues; O,O-dimethyl-, O,O-diethyl-, O,O-di-n-propyl-, O-methyl-O-ethyl-, O-methyl-O-n-propyl-, O-methyl-O-iso-propyl-, O-ethyl-O-n-propyl- and O-ethyl-O-iso-propyl-phosphoric acid diester chloride and the corresponding thiono analogues; O,S-dimethyl-, and O,S-diethyl-, O,S-di-n-propyl-, O,S-di-iso-propyl-, O-methyl-S-ethyl-, O-methyl-S-n-propyl-, O-methyl-S-iso-propyl-, O-ethyl-S-methyl-, O-ethyl-S-n-propyl-, O-ethyl-S-iso-propyl-, O-n-propyl-S-methyl-, O-n-propyl-S- ethyl-, O-n-propyl-S-iso-propyl-, O-iso-propyl-S-methyl-, O-iso-propyl-S-ethyl- and O-iso-propyl-S-n-propyl-thionophosphoric acid diester chloride and the corresponding thiono analogues; and O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-propyl-N-methyl-, O-n-propyl-N-ethyl-, O-n-propyl-N-n-propyl-, O-n-propyl-N-iso-propyl-, O-iso-propyl-N-methyl-, O-iso-propyl-N-ethyl-, O-iso-propyl-N-n-propyl- and O-iso-propyl-N-iso-propyl-phosphoric acid ester-amide chloride and the corresponding thiono analogues.

The starting compounds of the formula (II) are known.

The 2-cyclopropyl-4-hydroxy-pyrimidines also to be used as starting materials are defined by the formula (III). Preferably, in this formula, $R^2$ has the meaning stated to be preferred in connexion with formula (I).

The following may be mentioned specifically as examples of the starting compounds of the formula (III): 2-cyclopropyl-4-hydroxy-pyrimidine, 2-cyclopropyl-5-methyl-4-hydroxy-pyrimidine, 2-cyclopropyl-5-ethyl-4-hydroxy-pyrimidine, 2-cyclopropyl-5-n-propyl-4-hydroxy-pyrimidine, 2-cyclopropyl-5-iso-propyl-4-hydroxy-pyrimidine, 2-cyclopropyl-5-chloro-4-hydroxy-pyrimidine and 2-cyclopropyl-5-bromo-4-hydroxy-pyrimidine.

The starting compounds of the formula (III) have not been described hitherto in the literature. Compounds of the formula (III), in which $R^2$ represents hydrogen or alkyl, are obtained by reacting 2-ethoxy-acrylic acid halides or 2-ethoxy-1-alkyl-acrylic acid halides with cyclopropyl-amidine hydrochloride in the presence of an acid acceptor, for example triethylamine, and, if appropriate, in the presence of a diluent, for example acetonitrile, at temperatures between 0° and 50° C.

The 2-cyclopropyl-4-hydroxy-pyrimidine thus prepared can be converted into 5-chloro- or 5-bromo-2-cyclopropyl-4-hydroxy-pyrimidine by reaction with a halogen, in particular chlorine or bromine respectively, if appropriate in the presence of an acid acceptor, for example potassium hydroxide, and, if appropriate, in the presence of a diluent, for example water, at temperatures between 0° and 50° C.

The process for the preparation of the 2-cyclopropyl-pyrimidin-4-yl-(thiono)(thiol)-phosphoric (phosphonic) acid esters and ester-amides according to the invention is preferably carried out in the presence of a suitable solvent or diluent. Virtually any inert organic solvent can be used for this purpose, especially aliphatic and aromatic, optionally chlorinated, hydrocarbons, such as petrol, benzene, toluene, xylene, methylene chloride, chloroform, carbon tetrachloride, chlorobenzene and o-di-chlorobenzene; ethers, such as diethyl ether, dibutyl ether, tetrahydrofuran and dioxane; ketones such as acetone, methyl ethyl ketone, methyl isopropyl ketone and methyl isobutyl ketone; and nitriles, such as acetonitrile and propionitrile.

Any of the customary acid-binding agents can be used as the acid acceptor. Alkali metal carbonates and alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from −10° to +100° C., preferably at from 0° to 80° C. The process according to the invention is in general carried out under normal pressure.

To carry out the process according to the invention, the starting materials are usually employed in equimolar amounts. An excess of one or other reactant offers no substantial advantages. The reaction is in general carried out in a suitable diluent, in the presence of an acid acceptor, and the reaction mixture is stirred for several hours at the required temperature. Thereafter, an organic solvent, for example toluene, is added and the organic phase is worked up in the usual manner by washing, drying and distilling off the solvent.

The new compounds are obtained in the form of oils, which in a number of cases cannot be distilled without decomposition, but are freed from the last volatile constituents by so-called "incipient distillation", that is to say by prolonged heating under reduced pressure to moderately elevated temperatures, and are purified in this manner. They are characterized by the refractive index.

The 2-cyclopropyl-pyrimidin-4-yl-(thiono)(thiol)-phosphoric(phosphonic) acid esters and ester-amides according to the invention are distinguished by an excellent action as pesticides, especially by an insecticidal, acaricidal and nematicidal activity. They are active against plant pests, pests harmful to health and pests of stored products, and against estoparasites. They combine a low phytotoxicity with a good action against sucking and biting insects and mites.

For this reason, the compounds according to the invention can be employed successfully as pesticides in plant protection as well as in the hygiene field, the field of protection of stored products, and the veterinary medicine field.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all of some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci*;

from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Erisoma lanigerum, Hyalopterus arundinis, Macrosiphum avenae*, Myzus spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.;

from the order of the Lepidoptera, for example *Pectinophora gossypiella, Bupalus piniarius, Cheimatobia brumate, Lithocolletis blancardella, Hyponomeuta padella, Plutella maculipennis, Malacosoma neustria, Euproctis chrysorrhoea, Lymantria* spp., *Buccalatrix thurberiella, Phyllocnistis citrella*, Agrotis spp., Euxoa spp., Feltia spp., *Earias insulana, Heliothis* spp., *Laphygma exigua, Mamestra brassicae, Panolis flammea, Prodenia litura*, Spodopters spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Chloristoneura fumiferana, Clysia ambiguella, Homona magnanima* and *Tortrix viridana*;

from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., Meligethes aeneus, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*;

from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*;

from the order of the Siphonaptera, for example *Xenopsylla cheopis* and Ceratophyllus spp.;

from the class of the Arachnida, for example Scorpio maurus and *Latrodectus mactans*;

from the order of the Acarina, for example Acarus siro, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The plant-parasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp., and Trichodorus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects or acarids which comprises applying to said animals a compound according to the present invention, in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from ectoparasitical insects or acarids by the application to said animals of a compound according to the present invention, in admixture with a diluent or carrier.

The preparation of the novel compounds is shown in the following illustrative example:

EXAMPLE 1

(a)

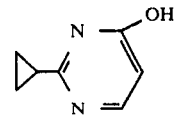

(a)

67.5 g (0.5 mol) of 2-ethoxyacrylic acid chloride were added dropwise, at 15°–20° C., to a mixture of 60.3 g (0.5 mol) of cyclopropionamidine hydrochloride, 101 g (1 mol) of triethylamine and 500 ml of acetonitrile, and the mixture was then stirred for a further 3 hours at room temperature. The solvent was then distilled off in vacuo, the residue was stirred twice with 500 ml of ethyl acetate at a time, the salt was filtered off and the filtrate was evaporated in vacuo. 42.9 g (64% of theory) of 2-cyclopropyl-4-hydroxy-pyrimidine were thus obtained in the form of colorless crystals of melting point 148° C.

(b)

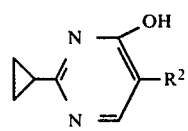

(b)

13.6 g (0.1 mol) of 2-cyclopropyl-4-hydroxy-pyrimidine were added to a solution of 5.6 g (0.1 mol) of potassium hydroxide in 100 ml of water. 16 g (0.1 mol) of bromine were then added dropwise at 15°–20° C., with slight cooling, and the mixture was stirred for a further hour at room temperature. The product which had precipitated was filtered off and rinsed with water. 15 g (70% of theory) of 2-cyclopropyl-4-hydroxy-5-bromo-pyrimidine were thus obtained in the form of colorless crystals of melting point 200° C.

The following compounds of the general formula

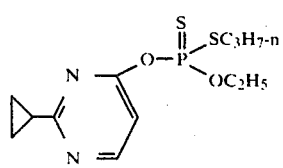

(II)

could be prepared analogously to (a) or (b):

TABLE 1

| Intermediate | $R^2$ |
|---|---|
| c | $CH_3$ |
| d | Cl |
| e | $C_3H_7$-iso |
| f | $C_2H_5$ |

(c)

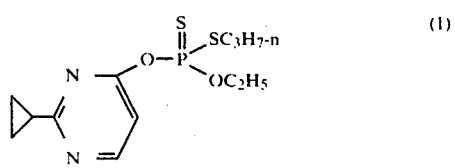

(1)

21.8 g (0.1 mol) of O-ethyl-S-n-propyl-thionothiolphosphoric acid ester chloride were added dropwise to a mixture of 13.6 g (0.1 mol) of 2-cyclopropyl-4-hydroxypyrimidine, 20.7 g (0.15 mol) of potassium carbonate and 300 ml of acetonitrile and the batch was allowed to react for a further 3 hours at 45°–50° C. Thereafter, the reaction mixture was cooled, poured into 500 ml of toluene and washed with water. The organic phase was then dried over sodium sulphate and freed from the solvent under reduced pressure, and the residue was subjected to incipient distillation. 22.8 g (72% of theory) of O-ethyl-S-n-propyl-O-(2-cyclopropyl-pyrimidin-4-yl)thionothiolphosphoric acid ester were obtained in the form of a yellow oil of refractive index $n_D^{22}$:1.5482.

The following compounds of the formula

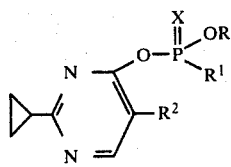

(I)

were obtained analogously:

TABLE 2

| Compound No. | R | $R^1$ | $R^2$ | X | Yield (% of theory) | Refractive index |
|---|---|---|---|---|---|---|
| 2 | $C_2H_5$ | $OC_2H_5$ | H | S | 76 | $n_D^{22}$: 1.5152 |
| 3 | $C_2H_5$ | $CH_3$ | H | S | 68 | $n_D^{22}$: 1.5373 |
| 4 | $C_2H_5$ | ⟨phenyl⟩ | H | S | 68 | $n_D^{22}$: 1.5812 |
| 5 | $CH_3$ | $OCH_3$ | H | S | 90 | $n_D^{20}$: 1.5249 |
| 6 | $C_2H_5$ | $NH-C_3H_7$-iso | H | S | 54 | $n_D^{23}$: 1.5268 |
| 7 | $C_3H_7$-n | $OC_2H_5$ | H | S | 91 | $n_D^{20}$: 1.5075 |
| 8 | $CH_3$ | $OC_3H_7$-n | H | S | 77 | $n_D^{24}$: 1.5264 |
| 9 | $C_2H_5$ | $OCH_3$ | H | S | 71 | $n_D^{24}$: 1.5293 |
| 10 | $C_2H_5$ | $OC_2H_5$ | Br | S | 60 | $n_D^{24}$: 1.5417 |
| 11 | $C_2H_5$ | ⟨phenyl⟩ | Br | S | | |
| 12 | $C_2H_5$ | $OC_2H_5$ | Cl | S | | |
| 13 | $C_2H_5$ | ⟨phenyl⟩ | Cl | S | | |
| 14 | $C_2H_5$ | $OC_2H_5$ | $CH_3$ | S | | |
| 15 | $C_2H_5$ | ⟨phenyl⟩ | $CH_3$ | S | | |
| 16 | $C_2H_5$ | $SC_3H_7$-n | $CH_3$ | S | | |
| 17 | $C_2H_5$ | $OC_2H_5$ | H | O | | |
| 18 | $C_2H_5$ | $OC_2H_5$ | $C_3H_7$-iso | S | | |
| 19 | $C_2H_5$ | $OC_2H_5$ | $C_2H_5$ | S | | |

The pesticidal activity of the compounds of this invention is illustrated by the following examples wherein the compounds according to the present invention are each identified by the number (given in brackets) from Example 1.

EXAMPLE 2

Drosophila test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all of the flies were killed; 0% meant that none of the flies were killed.

In this test, for example, the following compounds showed a superior activity compared to the prior art: (2), (3), (8), (9) and (10).

EXAMPLE 3

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of active compound of the desired concentration and were infested with caterpillars of the diamond-back moth (*Plutella maculipennis*), as long as the leaves were still moist.

After the specified periods of time, the degree of destruction was determined as a percentage: 100% meant that all of the caterpillars were killed whereas 0% meant that none of the caterpillars were killed.

In this test, for example, the following compounds showed a superior activity compared to the prior art:

(1), (2), (3), (4), (6), (8), (9) and (10).

EXAMPLE 4

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the conentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound of the desired concentration.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (1), (2), (3), (6), (8), (9) and (10).

EXAMPLE 5

LT$_{100}$ test for Diptera
Test insects: *Aedes aegypti*
Number of test insects: 25
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound used. The stated number of test insects was then placed in the Petri dish and the dish was covered with a glass lid.

The condition of the test insects was continuously observed. The time which was necessary for 100% "knockdown" was determined.

In this test, for example, the following compounds showed a superior action compared to the prior art: (1), (2) and (3).

EXAMPLE 6

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27 degrees C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

In this test, for example, the following compounds showed a superior activity compared to the prior art: (1), (2) and (6).

EXAMPLE 7

Test with parasitic fly larvae
Emulsifier: 80 parts by weight of alkylaryl polyglycol ether To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction was determined.

In this test, for example, the following compounds showed a superior action compared to the prior art: (1), (2) and (3).

EXAMPLE 8

Test with parasitic adult cattle ticks (*Boophilus microplus* res.)
Solvent: alkylaryl polyglycol ether To produce a suitable preparation of active compound, the active substance in question was mixed with the stated solvent in the ratio of 1:2 and the concentrate thus obtained was diluted with water to the desired concentration.

10 adult cattle ticks (*B. microplus* res.) were dipped for 1 minute into the active compound preparation to be tested. After transfer into plastic beakers and storage in a climatically controlled chamber, the degree of destruction was determined.

In this test, for example, the following compound showed a superior action compared to the prior art: (3).

It will be appreciated that the instant specification and examples are set forth by way of illustration and not limitation, and that various modifications and changes may be made without departing from the spirit and scope of the present invention.

What is claimed:

1. An O-alkyl-O-(2-cyclopropylpyrimidin-4-yl)-(thiono)(thiol)-phosphoric (phosphonic) acid ester or ester-amide of the formula

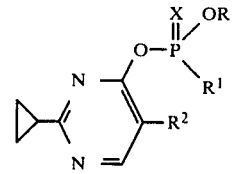

in which
R is alkyl with 1 to 5 carbon atoms,
R$^1$ is alkyl, alkoxy, alkylthio or alkylamino with 1 to 5 carbon atoms per alkyl radical, and
X is oxygen or sulphur.

2. A compound according to claim 1, wherein such compound is O-ethyl-S-n-propyl-O-(2-cyclopropyl-pyrimidin-4-yl)-thionothiol phosphoric acid ester of the formula

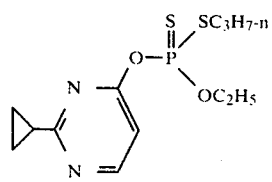

3. A compound according to claim 1, wherein such compound is O,O-diethyl-O-(2-cyclopropyl-pyrimidin-4-yl)-thionothiol phosphoric acid ester of the formula

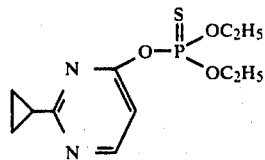

4. A compound according to claim 1, wherein such compound is O-ethyl-O-(2-cyclopropyl-pyrimidin-4-yl)-methanethionophosphonic acid ester of the formula

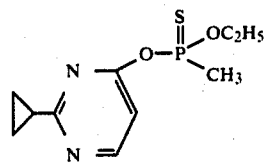

5. A compound according to claim 1, wherein such compound is O-ethyl-O-(2-cyclopropyl-pyrimidin-4-yl)-phenylthionophosphonic acid ester of the formula

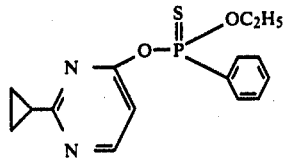

6. A compound according to claim 1, wherein such compound is O-methyl-O-n-propyl-O-(2-cyclopropyl-pyrimidin-4-yl)-thionothiol phosphoric acid ester of the formula

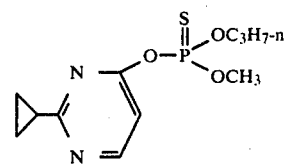

7. An arthropodicidal or nematicidal composition containing as active ingredient an arthropodicidally or nematicidally effective amount of a compound according to claim 1 in admixture with a diluent.

8. A method of combating arthropods or nematodes which comprises applying to the arthropods or nematodes, or to a habitat thereof, an arthropodicidally or nematicidally effective amount of a compound according to claim 1.

9. The method according to claim 8 wherein such compound is
O-ethyl-S-n-propyl-O-(2-cyclopropyl-pyrimidin-4-yl)-thionothiol phosphoric acid ester,
O,O-diethyl-O-(2-cyclopropyl-pyrimidin-4-yl)-thionothiol phosphoric acid ester,
O-ethyl-O-(2-cyclopropyl-pyrimidin-4-yl)-methanethionophosphonic acid ester,
O-ethyl-O-(2-cyclopropyl-pyrimidin-4-yl)-phenylthionophosphonic acid ester, or
O-methyl-O-n-propyl-O-(2-cyclopropyl)-pyrimidin-4-yl)-thionothiol-phosphoric acid ester, and such compound is applied to a domesticated animal.

* * * * *

UNITED STATES PATENT AND TRADEMARK OFFICE
CERTIFICATE OF CORRECTION

PATENT NO. : 4,261,983
DATED : Apr. 14, 1981
INVENTOR(S) : Fritz Maurer et al

It is certified that error appears in the above-identified patent and that said Letters Patent are hereby corrected as shown below:

Column 12, line 44  Delete "$-R^2$".

Signed and Sealed this

Sixth Day of October 1981

[SEAL]

Attest:

GERALD J. MOSSINGHOFF

Attesting Officer  Commissioner of Patents and Trademarks